United States Patent [19] [11] 4,071,025
Kohnke [45] Jan. 31, 1978

[54] LUNG-VENTING APPARATUS
[75] Inventor: Ole Bjorn Kohnke, Lyngby, Denmark
[73] Assignee: Ruth Lee Hesse, Piniehoj, Denmark
[21] Appl. No.: 614,953
[22] Filed: Sept. 19, 1975
[30] Foreign Application Priority Data
Sept. 20, 1974 Sweden .................................. 7411883
[51] Int. Cl.² ............................................. A61M 16/00
[52] U.S. Cl. .................. 128/145.7; 137/843; 251/367
[58] Field of Search .......................... 128/145.5–145.8, 128/142.2, 146.5; 137/525, 367; 251/367

[56] References Cited
U.S. PATENT DOCUMENTS

| | | | |
|---|---|---|---|
| 1,157,655 | 10/1915 | Mayer et al. | 128/145.7 |
| 2,428,451 | 10/1947 | Emerson | 128/145.7 |
| 2,902,992 | 9/1959 | Renvall | 128/145.7 |
| 3,083,707 | 4/1963 | Seeler | 128/145.8 |
| 3,106,204 | 10/1963 | Paramelle | 128/145.7 |
| 3,262,446 | 7/1966 | Stoner | 128/145.7 |
| 3,633,605 | 1/1972 | Smith | 137/525 |

Primary Examiner—Robert W. Michell
Assistant Examiner—Henry J. Recla
Attorney, Agent, or Firm—Spencer & Kaye

[57] ABSTRACT

A manually operated lung-venting apparatus includes a self-expanding bladder having a bladder inlet through which treating gas is drawn into the bladder during expansion thereof and a bladder outlet through which treating gas is driven out of the bladder during compression thereof. The apparatus further comprises a valve device having a housing attached to the bladder; an inlet chamber in the housing; a valve inlet for establishing communication between the bladder and the inlet chamber; a valve outlet which is in continuous communication with the inlet chamber and which is adapted to be connected to the respiratory system of a patient. The valve device further has a movable valve member supported in the housing and cooperating with the valve inlet to open or close the same; and a control mechanism connected to the movable valve member for moving and maintaining the movable valve member in its closed position when the pressure in the inlet chamber exceeds a predetermined value above the ambient pressure and for moving and maintaining the movable valve member in its open position when the pressure in the inlet chamber is below the predetermined value.

3 Claims, 5 Drawing Figures

LUNG-VENTING APPARATUS

BACKGROUND OF THE INVENTION

The invention relates to a manually operated lung-venting apparatus comprising a self-expanding bladder of the type having an inlet in one end wall and an outlet in the other end wall. The bladder by periodical compression and release enables breathing gas to be supplied into the lungs of a patient.

Such lung-venting systems fundamentally can belong to one of two different types, that is, open or closed systems. In the open system the pressure source is normally a so-called self-expanding venting bladder, i.e. a bladder which after compression automatically resumes its normal shape due to its inherent resiliency. The self-expanding bladder is provided with an inlet having a one-way suction valve and an outlet in communication with a three-way breathing valve. The outlet of the breathing valve is in communication with the lungs of the patient via a breathing mask or the like. When the bladder is compressed the suction valve is closed and the gas contained in the bladder is discharged through the breathing valve and via the breathing mask into the respiratory ducts of the patient. When the bladder is released after an insufflation process, it is re-filled with fresh gas through the suction valve while the patient is exhaling whereafter a new inhalation may be performed.

Closed lung-venting systems fundamentally comprise a closed circuit through which the breathing gas is flowing in a given direction with the aid of suitable one-way valves. In this case too, a compressible venting bladder is used in order to perform the insufflation, but the bladder, in this case, need not be completely self-expanding but may be adapted to be filled after a compression with fresh gas to some extent due to the pressure conditions prevailing in the system which is supplied with fresh breathing gas from a source of gas which is continously connected to the system.

In these and similar lung-venting systems it is necessary to protect the lungs of the patient against excessive venting pressures while at the same time care must be taken to supply the lungs under all conditions with adequate amounts of gas. In known systems the lungs ordinarily are protected by the provision of an excess pressure valve adapted to open at a predetermined pressure valve thereby to permit gas to be discharged from the system thus reducing the pressure therein.

An essential disadvantage of such systems resides in that the gas is discharged from the system when the excess pressure valve is opened which may mean that the remaining gas quantity is not sufficient to meet the patient's requirements. This condition is of particularly great importance in case the patient exhibits increased air duct resistance in front of the alveoli because the pressure drop across the air duct resistance may mean that the pressure within the system exceeds the opening pressure of the excess pressure valve before the alveoli have been sufficiently filled with gas; thus there is a great risk of an insufficient breathing-air supply to the patient.

Another disadvantage with these known systems comprising an excess pressure valve resides in that the treating gas is discharged into the environment which, on the one hand, means wastage of treating gas and, on the other hand, requires the provision of means for eliminating the outflowing treating gas which may be noxious.

The problems in connection with volume losses due to discharge of the treating gas into the environment through the excess pressure valve are of particularly great importance if a self-expanding venting bladder is used for lung-venting purposes because such bladders are characterized in that only a limited maximum pumping volume is at hand, which means that volume losses cannot be compensated for by unlimited increase of the pumping volume. As such self-expanding venting bladders, in addition, are of simple construction, it is not possible to measure in a simple way the proportion of the total pumping volume actually received within the lungs of the patient in comparison with the volume of the gas escaping into the environment. Thus the evaluation of the volume received by the lungs of the patient must be made in accordance with a subjective assessment which will yield fairly accurate results only after long experience.

SUMMARY OF THE INVENTION

It is an object of the invention to remove the above described drawbacks and to provide a manually operated lung-venting apparatus comprising a valve device preventing the lungs from being exposed to harmful excess pressures while at the same time no treating gas is discharged into the atmosphere and the lungs of the patient are filled with a gas volume which is exclusively determined by the lung/thorax characteristics of the patient and the predetermined control pressure but which is independent of the air duct resistance.

This object and others to become apparent as the specification progresses, are accomplished by the invention, according to which, briefly stated, the manually operated lung-venting apparatus includes a self-expanding bladder having a bladder inlet through which treating gas is drawn into the bladder during expansion thereof and a bladder outlet through which treating gas is driven out of the bladder during compression thereof. The apparatus further comprises a valve device having a housing attached to the bladder; an inlet chamber in the housing; a valve inlet for establishing communication between the bladder and the inlet chamber; a valve outlet which is in continuous communication with the inlet chamber and which is adapted to be connected to the respiratory system of a patient. The valve device further has a movable valve member supported in the housing and cooperating with the valve inlet to open or close the same; and a control mechanism connected to the movable valve member for moving and maintaining the movable valve member in its closed position when the pressure in the inlet chamber exceeds a predetermined value above the ambient pressure and for moving and maintaining the movable valve member in its open position when the pressure in the inlet chamber is below the predetermined value.

The operation of the lung-venting apparatus according to the invention when used in communication with the respiratory ducts of a patient is as follows:

When the bladder is compressed for introduction of gas into the patient, the treating gas will flow through the normally open valve device into the lungs of the patient. The predetermined closing pressure of the valve is normally not reached when the inhalation is correctly performed and when there is no abnormal air duct resistance. In the absence of either of these circumstances, the pressure may momentaneously exceed the closing value causing the valve to close thereby to prevent additional gas from passing through the valve. If the excess pressure was due only to an inhalation that was too rapid or to an abnormally strong resistance encountered in the breathing ducts of the patient, the pressure downstream of the valve will drop inasmuch as the treating gas penetrates further into the air ducts and after a short time the pressure will be below the closing pressure of the valve. This means that the valve will open again and an additional amount of treating gas will be permitted to flow through the valve and from there to the lungs. When the pressure again exceeds the closing pressure, the same procedure will be repeated until the lungs have been filled with an amount of treating gas causing the pressure downstream of the valve opening to assume an equilibrium condition equal to the closing pressure of the valve. The venting bladder can no longer be compressed by the operator who thus knows that the closing pressure now is prevailing throughout the lung alveoli of the patient. Accordingly, the operator will interrupt the insufflation and will release the bladder causing the operating pressure in the system to cease. As a result the valve will open, causing the pressure in the valve housing to drop and permitting the patient to exhale while the bladder expands and draws fresh treating gas. After termination of the exhaling phase of the patient, a new inhalation is performed and so on. As the valve is closed momentaneously when an inhalation is performed too strongly in relation to the air duct resistance, the operator will notice these interruptions of the gas supply from the fact that the bladder temporarily cannot be additionally compressed. In consideration thereof the operator can adapt the inhalation process to the air duct resistance of the patient. For this purpose it may even be suitable to use specific indicating means showing when the valve is closed and thus enabling the operator to adapt the rate of compressing the bladder to the conditions prevailing in the patient.

As appears from the explanations given above the closing pressure of the valve is to be chosen in such a way that the patient is not exposed to harmful excess pressures. The closing pressure may vary in respect to different categories of patients (adults, children, etc.). For adult patients it ordinarily will be of an order of magnitude of 30 – 40 cm $H_2O$ (overpressure). The closing mechanism is suitably constructed in such a way that the valve starts closing only when the overpressure approaches the closing pressure, for example at about 25 cm $H_2O$ when the closing pressure is about 30 cm $H_2O$.

In designing the valve according to the invention it is important to avoid substantial flow resistance of the valve in the open condition thereof because the patient should be in a position to inhale spontaneously from the system without undue strain.

As in certain emergency situations, such as in connection with nerve gas injuries, it is more important that the patient be supplied with a amount of treating gas rather than that the pressure be held at an optimum level, it is expedient to provide the valve with a device with the aid of which it may be held in an open position. Such an overriding device can also be valuable in order to avoid interruptions of operation in case the closing mechanism breaks down thus causing the valve to close at too low pressure. In such cases the operator may operate the disabling device and continue the treatment without interruption, the insufflation pressure being assessed on the basis of the resistance of the bladder against compression.

In accordance with a preferred embodiment, the valve device according to the invention comprises a movable membrane, one side of which is exposed to the pressure downstream of the valve opening whereas its other side is exposed to the ambient pressure. The membrane is connected with the valve closing element by means of a pin or the like. In this embodiment an overpressure in the system will shift the membrane towards the ambient pressure side, the valve closing element is moved from the normally open condition towards the closing position which is reached when the membrane has been moved a distance corresponding to the predetermined overpressure. In order to prevent the valve from starting its closing action before the overpressure approaches the predetermined valve, it is expedient to expose the membrane to the action of a device initially counteracting the overpressure and yielding to this overpressure — and thereby permitting the membrane and the valve element to start moving towards closing position — only when the overpressure approaches the predetermined value. This counteracting device may for example be a compression spring provided between the membrane and an abutment on the ambient pressure side of the membrane. When the valve element is in the closed position, it is also acted upon by the pressure differential between its both sides, i.e. between the driving pressure in the system on the upstream side and the pressure in the valve housing on the downstream side. Thus, in the closed position the force exerted on the valve closing element is determined, on the one hand, by the pressure force of the counteracting element and the pressure differential across membrane and, on the other hand, by the pressure differential across valve closing element itself. If the driving pressure in the lung-venting system is greater than the pressure in the valve housing, this pressure differential means that an additional force holds the valve element in the closed position. If, however, the driving pressure in the lung-venting system becomes lower than the pressure in the valve housing, which is the case when, for example, a self-expanding bladder is released after termination of the insufflation phase, the pressure differential will lift the valve element from its seat, thereby producing a pressure drop in the valve housing to a value which is lower than the closing pressure. As a result, the valve element will move to the open position under the action of the pressure force from the counteracting device.

The pin connecting the membrane with the valve closing element may advantageously extend through the membrane and project from the valve housing proper with the end not connected with the valve closing element. The pin thus serves as an indicating and overriding member. As the expose pin end moves outwardly when the valve is closed, the operator, by observing the movements of the pin end, will be able to determine whether the valve is closed or open and, accordingly, whether the insufflation is performed in the most suitable way. He then may take any necessary correcting step. If in an emergency situation insufflation is required to take place even with excess pressures greater than the predetermined maximum pressure, the operator will also be able to override the pressure limiting action by moving the free end of the pin inwardly and thereby holding the valve in the open position.

DESCRIPTION OF THE PREFERRED EMBODIMENT

Figure 1:
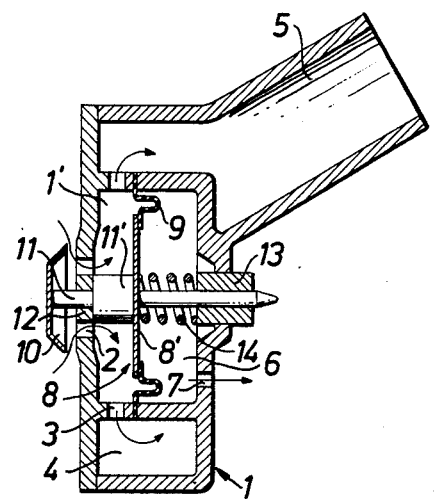
FIGS. 1 and 2 are schematical sections of a valve device for use in a lung-venting apparatus in respectively open and closed condition.
Figure 2:
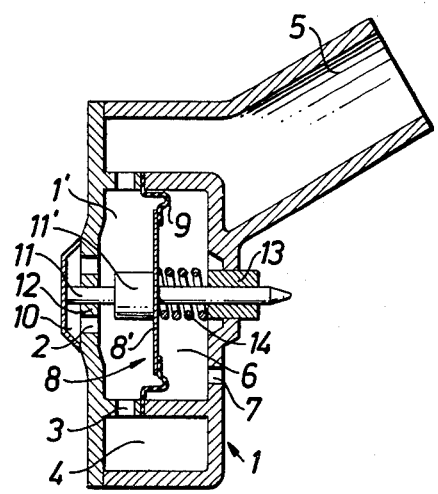

The valve device schematically shown in FIGS. 1 and 2 in a respectively open and closed condition and adapted to be combined, on the one hand, with a bladder 15 by insertion into an aperture in the one end wall thereof and, on the other hand, with a device such as a breathing mask or the like leading to the respiratory system of a patient comprises a valve housing 1 enclosing an inlet chamber 1' having one or more inlet ports 2 and one or more outlet ports 3. The outlet ports 3 open into a circular collecting chamber 4 which via a connecting stud 5 is adapted to be connected to a breathing mask or similar device leading to the respiratory system of the patient. The inlet port or ports 2 are, in a way to be described later in communication with the interior of a self-expanding bladder or the like such as the bladder 15 schematically illustrated in FIG. 3. Moreover, valve housing 1 encloses an additional chamber 6 which via a port 7 is in communication with the environment causing the ambient pressure continuously in chamber 6. An air-tight partition wall 8 separates chambers 1' and 6 from each other preventing gas from flowing between these chambers. The partition wall 8 is displaceable and it will be moved depending on the pressure differential between chambers 1' and 6 in a direction towards or away from the inlet port or ports 2. This mobility may be achieved in several conventional ways. In the embodiment shown the partition wall consists of a stiff central plate 8' surrounded by a resilient, preferably folded portion 9 permitting the pressure-dependent mobility of the partition wall 8. A movable valve member, such as a valve disk 10, positioned upstream of the inlet port 2 and cooperating therewith to open or open and close it depending on the pressure conditions prevailing in the system, is connected to a valve stem or valve pin 11. The latter extends from valve disk 10 through a low-friction guide 12, the first chamber 1', the central plate 8 of the partition wall and the second chamber 6. The free end of the pin is slidably supported in a bushing 13 in the outer wall of chamber 6, while the outer end of valve pin 11 extends outwardly from the bushing. Valve pin 11 is provided with an abutment 11' which in the rest position abuts against guide 12 and thereby limits the stroke of the valve pin. Plate 8' is sealingly attached to valve pin 11 and disk valve pin 11 and whereby disk valve 10 are shifted together with plate 8' of the partition wall with simultaneous extension of the elastic portion 9. Bushing 13 also forms an abutment for a compression spring 14 coiled about pin 11 in chamber 6 and also abutting against the partition wall 8 in the zone of the stiff plate 8'.

Figure 3:
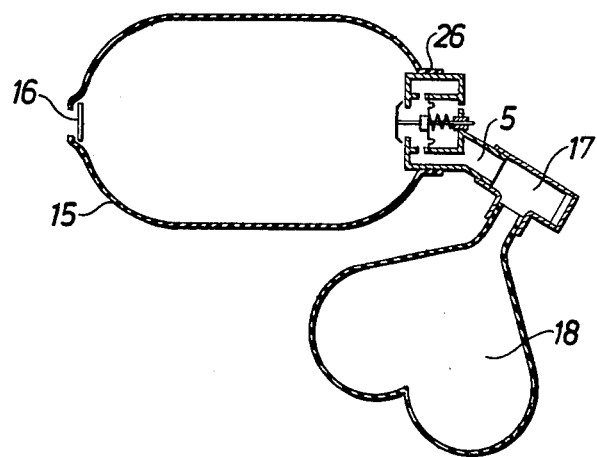
FIG. 3 in a schematical sectional view illustrates a self-expanding lung-venting bladder with attached valve device of the general type as shown in FIGS. 1 and 2.

In FIG. 3 there is schematically shown a self-expanding venting bladder 15 carrying a valve device in accordance with the invention. In a manner known by itself, the bladder 15 is provided with a one-way suction valve 16 for the treating gas inserted into one end wall of the bladder, whereas a pressure limiting valve according to the invention is inserted into the outlet opening 26 of the venting bladder. The connecting stud 5 is connected to a suitable three-way breathing valve 17 which in turn is in communication with the respiratory ducts of a patient, for example via a breathing mask 18 schematically shown.

The manually operated lung-venting apparatus as described above operates as follows:

In the absence of a pressure differential between chambers 1' and 6 the partition wall 8, 8', 9 assumes the position shown in FIG. 1 in which the spring 14 presses the abutment 11' of valve pin 11 against the guide 12 while valve disk 10 is in the open position. When by compression of the bladder 15 treating gas is blown through inlet port or ports 2, the gas will pass through chamber 1', the outlet openings 3, the collecting chamber 4 and the outlet stud 5 to be supplied to the patient. When an excess pressure appears in chamber 1' in relation to the ambient pressure prevailing in chamber 6, partition wall 8, 8', 9 will be actuated by a force tending to shift the wall towards chamber 6. However, this force is initially counteracted by the pre-tensioned compression spring 14. As the excess pressure in chamber 1' increases, the force acting on partition wall 8, 8', 9 is also increased. As soon as this pressing force exceeds the counteracting biasing force exerted by spring 14, the partition wall 8, 8', 9 — and thereby also valve pin 11 connected thereto as well as valve disk 10 — will start moving towards the closing position and as soon as the excess pressure reaches a predetermined value corresponding to the highest excess pressure to which the patient may be exposed, the valve pin and valve disk unit will have been moved so far towards chamber 6 that valve disk 10 will come into contact with its valve seat, thereby closing the inlet port or ports 2. This condition is illustrated in FIG. 2.

If closing pressure is prevailing in chamber 1' due to the fact that a corresponding pressure now is prevailing throughout the lung alveoli of the patient, the pressure in chamber 1' will remain constant and the inlet port or ports 2 will remain closed. This will be observed by the operator, on the one hand, on the basis of the fact that the venting bladder 15 cannot be compressed any longer and, on the other hand, from the fact that the protruding end of the valve pin remains in its extreme extended position; the operator now knows that the phase of insufflation is terminated, i.e. that the closing pressure is prevailing throughout the lung alveoli; accordingly he will release the bladder. As a result the driving pressure will fall below the pressure in chamber 1' and due to this pressure differential valve disk 10 will be urged to the open position. Due to said pressure differential, gas will flow out from chamber 1' through inlet ports 2 causing the pressure in chamber 1' to fall below the closing pressure. This in turn means that valve disk 10 will additionally move away from the closing position under the action of the return spring 14. When the pressure drop in chamber 1' which is in communication with the respiratory system of the patient, the patient will exhale while the bladder is filled with new treating gas either by self-expansion or at least in part by exhalation of the patient in closed systems (not illustrated). If, however, reaching the closing overpressure in chamber 1' is caused by the fact that the insufflation, i.e. the compression of the venting bladder, has been performed too quickly or that the respiratory duct resistance of the patient is too high, the pressure in chamber 1' will drop as the treating gas further penetrates into the respiratory ducts of the patient. This reduction in pressure causes the valve to open again, whereby treating is again supplied through inlet port or ports 2. For the reasons just indicated, the valve can again be closed and opened several times but eventually so much treating gas will have been supplied to the patient that the pressure in chamber 1' remains constant and equal to the closing pressure which the operator will observe as indicated above. Now the insufflation phase is terminated and the venting bladder is released enabling the patient to exhale and fresh treating gas is supplied to the bladder. As seen, for example, in FIGS. 1 and 2, that face of the valve disc 10 which is oriented outwardly (that is, towards the bladder 15) has an area which is smaller than the area of the movable partition wall face oriented towards the inlet chamber 1'. In the closed position of the valve disc 10 the latter is exposed, on opposite sides, to the pressure prevailing in the bladder 15 and the pressure prevailing in the inlet chamber 1'.

If in an emergency situation, such as in connection with nerve gas injuries, the operator wants to force treating gas into the patient in spite of the fact that the adjusted closing pressure is exceeded, he can in a simple way override the closing mechanism of the valve and hold the valve in an open position by pressing the protruding end of valve pin 11 in an inward direction. The same mode of operation can be used if, due to some fault, (such as breakage of the spring 14) the valve closes at pressure which obviously is too low. In this case the treatment may be continued without interruption by holding the valve open in the way as indicated. The operator has to judge the insufflation pressure in respect to the resistance of the venting bladder against compression.

As it is desirable that the flow resistance through the valve device according to the invention be as low as possible, the closure of the valve, i.e. the movement of the valve disk towards its seat, should preferably start only when the excess pressure in chamber 1' approaches the predetermined closing pressure. This effect which can be achieved in several ways, is obtained in the embodiment illustrated by means of the compression spring 14 which in the rest position is pretensioned towards partition wall 8, 8', 9 with a force which is slightly lower than the force acting on the partition wall 8, 8', 9 at the closing pressure. This may be obtained for example with the aid of a relatively soft spring having a relatively high load.

Figure 4:
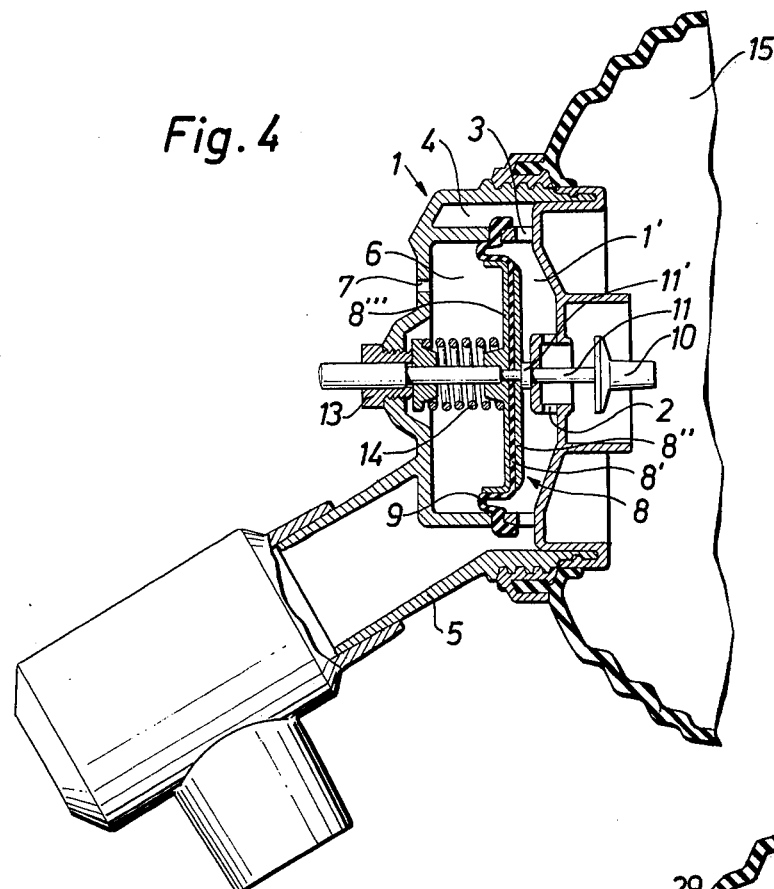
FIG. 4 is a sectional view of the outlet end wall portion of a self-expanding bladder carrying preferred embodiment shown in detail.
Figure 5:
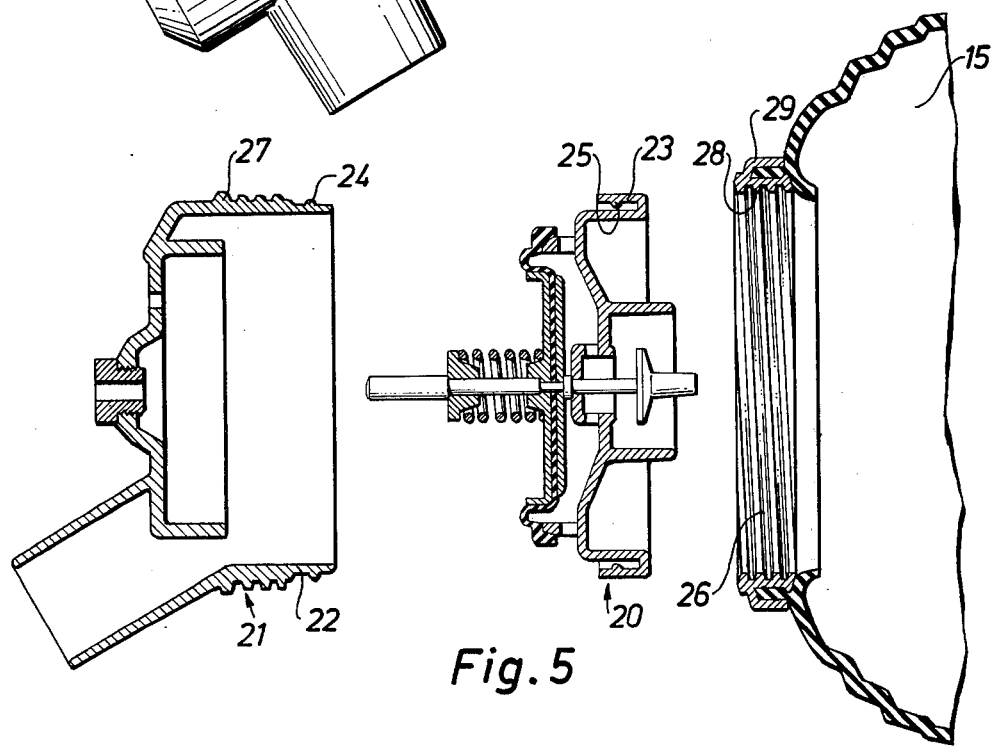
FIG. 5 is a sectional view of the outlet end wall portion of the bladder and the preferred embodiment of FIG. 4 in an exploded view.

An important aspect of the invention is illustrated in FIGS. 4 and 5. It is imperative that instruments of the type here in question be easily disassemblable without using tools and easy be to clean after use. The embodiment of a pressure limiting valve illustrated in FIGS. 4 and 5 in assembled and disassembled condition, respectively, satisfactorily complies with these requirements.

The embodiment shown in FIGS. 4 and 5 fully corresponds to the embodiment illustrated in FIGS. 1 and 2 and accordingly the same reference numbers are used in FIGS. 4 and 5 as in FIGS. 1 and 2.

It appears from FIGS. 4 and 5 that the pressure limiting valve is subdivided into two component parts, that an inlet portion 20 and an outlet portion 21. The outlet portion 21 defines an outlet chamber constituted by the stud 5. These two portions are substantially sealingly secured together by a snap-action connection in which a flange portion 22 of outlet valve portion 21 is inserted into a corresponding opposed grooved edge portion 23 on inlet valve portion 20. The mutual engagement between the two valve portions 20 and 21 is improved by the provision of opposed ridges such as an outwardly facing ridge 24 on the flange 22 of outlet portion 21 and an inwardly facing ridge 25 on the outer wall bounding the flange-receiving groove 23 of inlet valve portion 20. It is apparent that the connection between valve portions 20 and 21 may be of any other suitable type such as inner and outer screw threads on opposed surfaces of the two valve portions.

As appears from FIG. 5, all the movable parts of the valve mechanism are carried by the inlet valve portion 20. As soon as the two portions are assembled, for example by pressure-fitting, threaded engagement or otherwise, the valve chambers and the valve mechanism are ready for use, with the free end of valve pin 11 extending through bushing 13 opposite the valve disc 10.

Partition wall 8 is here shown to comprise a rubber disk 8' having a circumferential pleat 9 and a central portion rigidly held between disk elements 8" and 8'''. The thickened outermost edge of rubber disk 8' forms a sealing gasket delimiting chamber 1' from chamber 6 in the assembled condition of the valve portions 20 and 21 as clearly shown in FIG. 4.

The assembled pressure limiting valve 20, 21 is inserted into the outlet opening 26 formed in the end wall of bladder 15 by engagement between an outer thread 27 on valve portion 21 and an inner thread 28 formed on a relatively stiff wall portion 29 sealingly surrounding the outlet opening 26. For obvious reasons the largest diameter of the circular valve inlet portion 20 is smaller than the free aperture within the inner thread 28 bounding the outlet aperture 26 in the end wall of bladder 15.

A very important secondary advantage realized by the construction described with by reference to FIGS. 4 and 5 resides in the fact that in the disengaged state of valve portions 20 and 21 no parts are under any tension whatsoever. If, as customary in this art the valve constructions are made from plastic material, any tension left in disassembled parts during sterilization might involve the risk of their permanent deformation. No such risk will be encountered during a cleaning treatment performed on the disassembled parts 20 and 21 of the pressure limiting valve of FIGS. 4 and 5.

It is to be understood that the invention is not restricted to the specific embodiments described above: many variations and modifications are imaginable within the frame of the basic inventive idea. For example, it is not necessary that the members controlling the closing and opening of the valve as a function of the pressure differential prevailing between the first chamber 1' and the environment be constructed as specifically shown. It is feasible to use any pressure sensing and controlling member performing the functions described. Moreover, for example, it is not necessary that the valve construction comprises a particular second chamber; instead, the partition wall 8, 8', 9 may be in direct communication with the environment. Also, the specifically shown embodiments of the partition wall can be varied in many respects.

What I claim is:

1. In a manually operated lung-venting apparatus including a self-expanding bladder having a bladder inlet through which treating gas is drawn into the bladder during expansion thereof; a bladder outlet through which treating gas is driven out of the bladder during compression thereof and a three-way breathing valve having an inlet in communication with the bladder outlet and an outlet to be connected to the respiratory system of a patient; the improvement comprising, in combination, a valve device having a. a housing having first, second and third housing portions;
b. a first mounting means for releasably securing said first and second housing portions to one another; said first mounting means being formed of cooperating first and second ridges carried, respectively, by said first and second housing portions for providing a snap-in engagement between said first and second housing portions, by engagement of said first and second ridges behind one another;
c. a second mounting means for sealingly securing said third housing portion to said bladder in the zone of said bladder outlet;
d. a third mounting means for sealingly and releasably securing said first and second housing portions to said third housing portion; said third mounting means including an inner thread formed on said third housing portion and an outer thread complemental with said inner thread and formed on said second housing portion;
e. means defining an inlet chamber in said first housing portion;
f. means defining a valve inlet in said first housing portion; said valve inlet being connected to said bladder outlet for establishing communication between said bladder and said inlet chamber;
g. means defining a valve outlet in said first housing portion; and means defining an outlet chamber in said second housing portion; said valve outlet being in continuous communication with said outlet chamber; said outlet chamber being connected to the inlet of said three-way breathing valve;
h. a movable valve member supported in said first housing portion adjacent said valve inlet for opening and closing said valve inlet; said movable valve member having an open position in which communication is maintained between said bladder and said inlet chamber and a closed position in which gas flow is blocked from said bladder to said inlet chamber; and
i. control means arranged in said first housing portion and connected to said movable valve member for moving and maintaining said movable valve member in said closed position when the pressure in said inlet chamber exceeds a predetermined value above the ambient pressure and for moving and maintaining said movable valve member in said open position when the pressure in said inlet chamber is below said predetermined value; said first housing portion forming a structural unit with said movable valve member and said control means.

2. The lung-venting apparatus as defined in claim 1, wherein said first, second and third housing portions have a circular configuration and are arranged coaxially in an assembled state of the valve device.

3. In a manually operated lung-venting apparatus including a self-expanding bladder having a bladder inlet through which treating gas is drawn into the bladder during expansion thereof; a bladder outlet through which treating gas is driven out of the bladder during compression thereof and a three-way breathing valve having an inlet in communication with the bladder outlet and an outlet to be connected to the respiratory system of a patient; the improvement comprising, in combination, a valve device having a. a housing having first and second housing portions;
b. a first mounting means for releasably securing said first and second housing portions to one another;
c. a second mounting means for releasably and sealingly securing said first and second housing portions to said bladder outlet;
d. means defining an inlet chamber in said first housing portion;
e. means defining a valve inlet in said first housing portion; said valve inlet being connected to said bladder outlet for establishing communication between said bladder and said inlet chamber;
f. means defining a valve outlet in said first housing portion; and means defining an outlet chamber in said second housing portion; said valve outlet being in continuous communication with said outlet chamber; said outlet chamber being connected to the inlet of said three-way breathing valve;
g. a movable valve member supported in said first housing portion adjacent said valve inlet for opening and closing said valve inlet; said movable valve member having an open position in which communication is maintained between said bladder and said inlet chamber and a closed position in which gas flow is blocked from said bladder to said inlet chamber; and
h. control means arranged in said first housing portion and connected to said movable valve member for moving and maintaining said movable valve member in said closed position when the pressure in said inlet chamber exceeds a predetermined value above the ambient pressure and for moving and maintaining said movable valve member in said open position when the pressure in said inlet chamber is below said predetermined value; said first housing portion forming a structural unit with said movable valve member and said control means.

* * * * *